United States Patent [19]
Edelson et al.

[11] Patent Number: 5,651,993
[45] Date of Patent: Jul. 29, 1997

[54] SPECIFIC IMMUNE SYSTEM MODULATION

[75] Inventors: Richard L. Edelson, Westport; Francis P. Gasparro, Hamden; Robert E. Tigelaar, Guilford, all of Conn.

[73] Assignee: Yale University, New Haven, Conn.

[21] Appl. No.: 977,672

[22] Filed: Nov. 18, 1992

[51] Int. Cl.$^6$ ............................................. A61K 35/14
[52] U.S. Cl. ...................... 424/534; 514/825; 514/866; 424/85.7
[58] Field of Search ...................... 435/244, 240.1; 424/88, 89, 92, 93 R, 934, 93 V, 93 W, 85.1, 85.5, 85.6, 85.7, 534; 514/825, 866

[56] References Cited

U.S. PATENT DOCUMENTS

| | | | |
|---|---|---|---|
| 4,684,521 | 8/1987 | Edelson et al. | 424/101 |
| 4,838,852 | 6/1989 | Edelson et al. | 604/4 |
| 5,114,721 | 5/1992 | Cohen et al. | 424/534 |
| 5,147,289 | 9/1992 | Edelson et al. | 604/4 |

OTHER PUBLICATIONS

Malawista, et. al. 1991. Annals New York Acad. Sci. pp. 217–225.
Osbaird, M.E. 1990. Immunol. Today 11: 193–195.
Edelson, et al. 1991. Annals New York Acad. Sci. 636: 154–164.
*Fundamental Immunology* $2^{nd}$ ed Raven Press W. Paul. 1989 pp. 546–567.
Cohen et al. Science 262: 841–843 Nov. 5, 1993.
Edelson, R., "Photopheresis: A Clinically Relevant Immunobiologic Response Modifier," Annals of N.Y. Academy of Sciences 636:154–164 (1991).
Ljunggren et al., "Empty MHC class 1 molecules come out in the cold," Nature 346:476–480 (1990).
Rock et al., "Reassociation with $\beta_2$–microglobulin is necessary for Kb class 1 major histocompatibility complex binding of exogenous peptides," Proc. Natl. Acad. Sci. (USA) 87:7517–7521 (1990).
Essential Immunology, seventh edition, Blackwell Scientific Publications, Oxford, Great Britain, pp. 26–31 and 140–150 (1991) (Roitt).
Edelson, R., "Light–activated Drugs," Scientific American 256(8):68–75 (1988).
Rook, A., "Photopheresis in the Treatment of Autoimmune Disease: Experience with Pemphigus Vulgaris and Systemic Sclerosis," Annals of N.Y. Academy of Science 636:209–216 (1991).
Malawista, S., et al., "Photopheresis for Rheumatoid Arthritis," Annals of N.Y. Academy of Science 636:217–226 (1991).
Perez, M., et al., "Inhibition of Antiskin Allograft Immunity Induced by Infusions with Photoinactivated Effector T Lymphocytes (PET Cells); The Congenic Model," Transplantation 51:1283–1289 (1991).
Bisaccia, E., et al., "Viral–Specific Immunization in AIDS–Related Complex by Photopheresis," Annals of N.Y. Academy of Science 636:321–330 (1991).
Ben–Nun, A., et al., "Vaccination against autoimmune encephalomyelitis with T lymphocyte line cells reactive against myelin basic protein," Nature 292:60–61 (1981).
Holoshitz, J., et al., "Lines of T lymphocytes induce or vaccinate against autoimmune arthritis," Science 219:56–58 (1983).
Lider, O., et al., "Anti–idiotypic network induced by T cell vaccination against experimental autoimmune encephalomyelitis," Science 239:181–183 (1988).
Khavari, P., et al., "Specific vaccination against photoinactivated cloned T cells," Abstract Clin. Res. 36:662A (1988).
Edelson, R., et al., "Treatment of cutaneous T cell lymphoma by extracorporeal photochemotherapy," N. Engl. J. Med. 316:297–303 (1987).
Boon, P., "Toward a Genetic Analysis of Tumor Rejection Antigens" Adv. Cancer Res. 58:177–210 (1992).
Latron, F., "A Critical Role for Conserved Residues in the Cleft of HLA–A2 in the Presentation of a Nonapeptide to T–cells," Science 257:964–967 (1992).
Malane, M. and Gasparro, R., "T Cell Molecular Targets for Psoralens," Annals of N.Y. Academy of Science 636:196–208 (1991).
Heald, P.W., "Photopheresis for Cutaneous T Cell Lymphoma," Annals New York Academy of Sciences 636:171–177 (1991).
Calzavara–Pinton, et al., "A Reappraisal of the Use of 5–Methoxy–psoralen in the Therapy of Psoriasis," Exptl. Dermatol. 1:46–51 (1992).
Yang, et al., "8–MOP DNA Photoadducts in Patients Treated with 8–MOP and UVA," J. Invest. Dermatol. 92:59–63 (1989).
Berger, C., et al., "Comparison of Synthetic Psoralen Derivatives and 8–MOP in the Inhibition of Lymphocyte Proliferation," Annals of N.Y. Academy of Science 453:80–90 (1985).
Jenkins, M.K., "The Role of Cell Division in the Induction of Clonal Anergy," Immunology Today 13:69–73 (1992).
Gerometta, J.S., et al., "UVB radiation inactivates a co–stimulatory factor expressed on the surface of Langerhans cells, thus rendering them capable of inducing clonal anergy in CD4+ cells," J. Invest. Dermatol. 96:626 (abstract) (1991).
van Iperen, H.P. and Beijersbergen van Henegouwen, "An animal model for extracorporeal photochemotherapy based on contact hypersensitivity," J. Photochem. Photobiol. B:Biol. 15:361–366 (1992).

(List continued on next page.)

*Primary Examiner*—Lila Feisee
*Assistant Examiner*—Minh-Tam B. Davis
*Attorney, Agent, or Firm*—Wolf, Greenfield & Sacks P.C.

[57] ABSTRACT

Methods and pharmaceutical compositions for modifying the immune response of a mammal to a specific antigen are provided. The methods include treating an antigen presenting cell to enhance expression of a major histocompatibility complex molecule and reacting the treated antigen presenting cell with the antigen extracorporeally to form an antigen-associated antigen presenting cell.

12 Claims, 1 Drawing Sheet

OTHER PUBLICATIONS

Berger, C.L., et al., "Autoregulation of the Immune Response in Autoimmune Disease and Cardiac Transplantation by Photoinactivated Autologous Lymphocytes," Annals New York Academy of Sciences 636:246–278 (1991).

van Pel, A., et al., "Tum–Antigens, TSTA, and T Cell Immune Surveillance," Annals New York Academy of Sciences 636:43–51 (1991).

Tsomides, T. et al., Naturally Processed Viral Peptides Recognized by Cytotoxic T Lymphocytes on Cells Chronically Infected by Human Immunodeficiency Virus Type 1, J. Exp. Med. 180:1283–1293 (1994).

Kannagi, M. et al., Expression of the Target Antigen for Cytotoxic T Lymphocytes on Adult T–cell Leukemia Cells, Int. J. Cancer 54:582–588 (1993).

Roitt, I., Essential Immunology, 7th Ed., Blackwell Scientific Publications, Oxford, England, 1991, pp. 120–127.

FIG. 1

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( D ) TOPOLOGY: linear     ( i i ) MOLECULE TYPE: peptide     ( i i i ) HYPOTHETICAL: NO     ( i v ) ANTI-SENSE: NO     ( v i ) ORIGINAL SOURCE:
        ( A ) ORGANISM: mouse     ( x i ) SEQUENCE DESCRIPTION: SEQ ID NO:1:

Ile  Ser  Thr  Gln  Asn  Arg  Arg  Ala  Leu  Asp  Val  Ala
    1                      5                              10

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( D ) TOPOLOGY: linear     ( i i ) MOLECULE TYPE: peptide     ( i i i ) HYPOTHETICAL: NO     ( i v ) ANTI-SENSE: NO     ( v i ) ORIGINAL SOURCE:
        ( A ) ORGANISM: mouse     ( x i ) SEQUENCE DESCRIPTION: SEQ ID NO:2:

Ile  Ser  Thr  Gln  Asn  His  Arg  Ala  Leu  Asp  Val  Ala
    1                      5                              10

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( i i i ) HYPOTHETICAL: NO     ( i v ) ANTI-SENSE: NO     ( v i ) ORIGINAL SOURCE:
        ( A ) ORGANISM: mouse     ( x i ) SEQUENCE DESCRIPTION: SEQ ID NO:3:

Gly  Pro  His  Ser  Ser  Asn  Phe  Gly  Tyr
    1                      5

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear (i i) MOLECULE TYPE: peptide (i i i) HYPOTHETICAL: NO (i v) ANTI-SENSE: NO (v i) ORIGINAL SOURCE:
    (A) ORGANISM: mouse (x i) SEQUENCE DESCRIPTION: SEQ ID NO:4:

```
Gly   Pro   His   Ser   Asn   Asn   Phe   Gly   Tyr
 1                       5
```

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: linear     (i i) MOLECULE TYPE: peptide     (i i i) HYPOTHETICAL: NO     (i v) ANTI-SENSE: NO     (v i) ORIGINAL SOURCE:
        (A) ORGANISM: mouse     (x i) SEQUENCE DESCRIPTION: SEQ ID NO:5:

```
Lys   Tyr   Gln   Ala   Val   Thr   Ala   Thr   Leu   Glu   Glu
 1                       5                                  10
```

(2) INFORMATION FOR SEQ ID NO:6:

(i) SEQUENCE CHARACTERISTICS:
        (A) LENGTH: 11 amino acids
        (B) TYPE: amino acid
        (D) TOPOLOGY: linear     (i i) MOLECULE TYPE: peptide     (i i i) HYPOTHETICAL: NO     (i v) ANTI-SENSE: NO     (v i) ORIGINAL SOURCE:
        (A) ORGANISM: mouse     (x i) SEQUENCE DESCRIPTION: SEQ ID NO:6:

```
Lys   Tyr   Gln   Ala   Val   Thr   Thr   Thr   Leu   Glu   Glu
 1                       5                                  10
```

(2) INFORMATION FOR SEQ ID NO:7:

(i) SEQUENCE CHARACTERISTICS:
        (A) LENGTH: 13 amino acids
        (B) TYPE: amino acid
        (D) TOPOLOGY: linear     (i i) MOLECULE TYPE: peptide     (i i i) HYPOTHETICAL: NO     (i v) ANTI-SENSE: NO     (v i) ORIGINAL SOURCE:
        (A) ORGANISM: mouse     (x i) SEQUENCE DESCRIPTION: SEQ ID NO:7:

```
Glu   Ile   Leu   Pro   Leu   Gly   Trp   Leu   Val   Phe   Ala   Val   Val
 1                       5                                  10
```

(2) INFORMATION FOR SEQ ID NO:8:

(i) SEQUENCE CHARACTERISTICS:
        (A) LENGTH: 13 amino acids
        (B) TYPE: amino acid
        (D) TOPOLOGY: linear     (ii) MOLECULE TYPE: peptide     (iii) HYPOTHETICAL: NO     (iv) ANTI-SENSE: NO     (vi) ORIGINAL SOURCE:
        (A) ORGANISM: mouse     (xi) SEQUENCE DESCRIPTION: SEQ ID NO:8:

Glu Ile Leu Pro Leu Gly Trp Leu Ala Phe Ala Val Val
1               5                   10

SPECIFIC IMMUNE SYSTEM MODULATION

GOVERNMENT SUPPORT

This invention was made with government support under Contract No. 2R01CA43058-09A1 awarded by the National Institutes of Health. The government has certain rights in the invention.

FIELD OF THE INVENTION

This invention relates to methods and pharmaceutical compositions for specifically modifying an immune response to an antigen. The methods include treating an antigen presenting cell to enhance expression of the major histocompatibility complex molecules, followed by reacting the treated antigen presenting cells with an antigen extracorporeally to form an antigen-associated antigen presenting cell.

BACKGROUND OF THE INVENTION

Immune system responses may be classified as humoral or cell-mediated. A humoral response is mediated by B lymphocytes in the form of freely diffusible antibody molecules. A cell-mediated response is mediated by specifically reactive lymphocytes, such as T lymphocytes ("T cells"), rather than antibodies.

T cells react with foreign antigens via surface receptors that are distinctive for each T cell clone. The T cell surface receptors are generally composed of two disulfide-linked protein chains having unique amino acid sequences (Edelson, R., "Photopheresis: A Clinically Relevant Immunobiologic Response Modifier", *Annals of N.Y. Academy of Sciences* 636:154–164 (1991). The physical properties of these receptors confer specific binding capabilities and permit each of the several million clones of T cells in an individual to operate independently.

The T cell receptor is capable of recognizing a particular antigen only when it is associated with a surface marker on an antigen presenting cell, such as a macrophage. The surface markers belong to a group of molecules known as the major histocompatibility complex (MHC). Binding of the T cell receptor to the antigen on the antigen presenting cell induces changes in the T cell, which changes collectively comprise the cell-mediated response.

The induction of expression of "empty", i.e., devoid of peptide, major histocompatibility complex class I molecules under conditions of reduced temperature has been demonstrated in a murine lymphoma mutant cell line (Ljunggren et al., *Nature* 336:476–480 (1990)). The mutant cell line lacks the appropriate intracellular mechanism for loading intracellular peptides into the binding clefts of newly synthesized class I molecules. The mutant cell line class I molecules are substantially empty and thermodynamically unstable at 37° C., but are stabilized by providing an exogenous source of peptides which bind to the empty class I molecules. An increased level of major histocompatibility complex class I expression has also been reported for a corresponding wild-type cell line (ibid.) when grown at temperatures below 37° C. However, the tests used to identify class I expression in that system did not distinguish between empty class I and class I molecules associated with peptide.

Improvement in the relatively inefficient exchanging of an exogenously added peptide for peptides already present in the clefts of class I molecules by the addition of exogenous free beta-2-microglobulin has also been demonstrated (Rock et al., *PNAS (USA)* 87:7517–7521 (1990).

Two signals are primarily responsible for inducing the T cell mediated response to an antigen presenting cell which is associated with antigen. A first signal is due to binding of the T cell to the antigen on the antigen presenting cell. A second, co-stimulatory signal is sent by "accessory" membrane molecules or soluble messengers from the antigen presenting cell to the responding T cell. These soluble intercellular messengers regulate the amplitude and duration of the immune response and are given the generic term, cytokines. Cytokines include the group previously referred to as lymphokines, monokines, interleukins and interferons (*Essential Immunology*, seventh edition, Blackwell Scientific Publications, Oxford, Great Britain, 1991, pp. 140–150). If the antigen presenting cell does not send the second signal, the T cell is effectively paralyzed, i.e., unable to mount an immune response to the antigen. Certain types of antigen presenting cells, e.g., resting T cells, are unable to send the second signal. Accordingly, in the absence of exogenous cytokine or other second signal, such resting T cells which function as antigen presenting cells downregulate an immune response to the presented antigen and lead to antigen specific immunologic paralysis of the T cell whose membrane receptor has been engaged.

T cells also function in regulation of an immune response via recognition by the immune system of the T cell surface receptor. Thus, several studies, described herein, have suggested that the ability of the immune system to recognize the receptor of an aberrant T cell clone as antigenic makes possible the vaccination of a patient against a pathogenic clone of T cells.

Cutaneous T cell lymphoma (CTCL) is an example of an immune system disease that is caused by a massive expansion of a single clone of aberrant T cells. Extracorporeal photochemotherapy ("photopheresis") for the treatment of cutaneous T cell lymphoma has been described (Edelson, R., "Light-activated Drugs", *Scientific American* 256(8): 68–75 (1988); Edelson, R., "Photopheresis: A Clinically Relevant Immunobiologic Response Modifier", *Annals of N.Y. Academy of Sciences* 636:154–164 (1991). The treatment comprises isolating the patient's T cells, irradiating the cells in the presence of a photoactivatable agent (8-MOP) and reinfusing the damaged T cells. The 8-MOP is activated by the ultraviolet light to form a transient molecule capable of photomodifying cellular DNA. This therapy reportedly results in selective destruction of the malignant T cell clone.

It is believed that exposure of the malignant clone to 8-MOP and ultraviolet light, followed by return of the irradiated, damaged cells to the patient, elicits a specific response to the aberrant T cells that is mediated by T cell surface receptors, i.e., the damaged cells of the malignant clone had, in effect, primed the immune system to specifically destroy the clone. In essence, photopheresis "vaccinated" the CTCL patients against their own cancer.

Photopheresis has also been used for the treatment of several autoimmune disorders, including pemphigus vulgaris and systemic sclerosis (Rook, A., "Photopheresis in the Treatment of Autoimmune Disease: Experience with Pemphigus Vulgaris and Systemic Sclerosis", *Annals of N.Y. Academy of Science* 636:209–216 (1991) and rheumatoid arthritis (Malawista, S., et al., "Photopheresis for Rheumatoid Arthritis", *Annals of N.Y. Academy of Science* 636:217–226 (1991).

U.S. Pat. No. 4,838,852, issued to Edelson et al. (hereinafter Edelson '852), the contents of which are incorporated herein by reference, describes a method for altering the immune system response of a mammal to an antigen. The Edelson '852 method comprises (a) contacting the subject's immune system with the specific antigen for a suitable time to artificially stimulate the immune system, (b) withdrawing antigen-stimulated blood cell material from the subject, (c) treating the withdrawn material to alter the antigen-stimulated cells, and (d) returning the treated material to the subject. Contacting the subject's immune system with the specific antigen is achieved in any manner which introduces the antigen into the mammal's immune system, e.g., by injecting directly into the blood stream, the lymphatic system or the lymphoid organs. Edelson '852 also discloses that it may be possible to render the cells incapable of recognizing an antigen by withdrawing the blood cell containing material from the subject, treating the withdrawn material as above, returning the treated material to the subject and then contacting the subject's immune system with a specific antigen.

U.S. Pat. No. 5,147,289, issued to Edelson (hereinafter Edelson '289), the contents of which are incorporated hereinby reference, describes methods for non-specifically enhancing the immune system response of a mammal to an antigen. The method comprises (A) enhancing the immune system response by (a) withdrawing leukocyte containing material from the mammal, (b) treating the withdrawn leukocytes in a manner to alter the cells, (c) returning the treated leukocytes to the mammal and (B) artificially contacting the mammal's immune system with the antigen for a suitable period of time to stimulate an immune system response.

With respect to the Edelson '852 and '289 patents, the withdrawn leukocytes may be altered by, for example, inactivating the cells by photopheresis, exposing the cells to high or low temperature, high or low pH values, high or low pressure, hypotonic solutions, chemotherapeutic agents, or a variety of other inactivating conditions.

Photopheresis also has been used prophylactically to prevent graft rejection by injecting into mice a preparation containing Photoinactivated Effector T ("PET") cells (Perez, M. et al., "Inhibition of Antiskin Allograft Immunity Induced by Infusions with Photoinactivated Effector T Lymphocytes (PET Cells); "The Congenic Model", *Transplantation* 51:1283–1289 (1991). To prepare the PET cells, T cell clones mediating skin graft rejection were expanded in vivo and photoinactivated using 8-MOP. Perez et al. report that this procedure results in the adoptive transfer of tolerance for skin allotransplantation, as demonstrated by prolongation of allograft survival in the recipients of PET cells.

A preliminary study to evaluate the potential therapeutic value of photopheresis in seven patients with AIDS-related complex (ARC) has been reported (Bisaccia, E. et al., "Viral-Specific Immunization in AIDS-Related Complex by Photopheresis", *Annals of N.Y. Academy of Science* 636:321–330 (1991). One advantage of photopheresis for the treatment of an immunocompromised patient, such as an AIDS patient, is that unlike antiviral drug treatments, extracorporeal photopheresis spares the tissue-fixed elements of the immune system from exposure to the therapy, thereby minimizing damage to the antigen processing system.

Photopheresis has been demonstrated to produce a generalized clinical benefit for a variety of autoimmune diseases that are characterized by a disorder in T cell regulation. In addition to producing an immunization effect against clones of autoreactive T cells, photopheresis may also result in induction of soluble extracellular messengers, e.g., tumor necrosis factor, which have a therapeutic adjuvant effect for a number of disease states.

The above-described therapies have in common the ability to vaccinate against a particular T cell activity without isolating or identifying the clone(s) responsible for the activity. None of the cited references and/or patents disclose a method for specifically regulating an immune system response. Accordingly, there is still a need for methods and pharmaceutical compositions to precisely regulate the immune system response to a specific antigen. Such methods would permit stimulation of a competent or incompetent immune system and would permit the stimulation of an immune system in a subject already weakly stimulated with the antigen. Preferably, such methods and compositions would permit stimulation of the immune system in the form of booster immunizations.

SUMMARY OF THE INVENTION

The present invention provides methods and pharmaceutical compositions for specifically modifying an immune system response to an antigen. In particular, the invention provides methods and compositions for actively immunizing patients against malignant cells or lymphocytes responsible for autoimmune disease. Also provided are methods for inducing immunologic tolerance to autologous or exogenous antigens and compositions useful in suppressing clinically undesirable immunologic reactions.

According to one aspect of the invention, a method for forming an antigen-associated antigen presenting cell is provided. The method comprises treating a preparation containing an antigen presenting cell to enhance expression by the cell of a major histocompatibility complex molecule and reacting the treated antigen presenting cell with the antigen extracorporeally to form an antigen-associated antigen presenting cell. In a preferred embodiment, the antigen presenting cells are T cells which have been treated to enhance expression of the major histocompatibility complex class I molecules and the antigens are peptides. The peptide antigens are associated with a solid tumor malignancy, an immunodeficiency disease or a hypersensitivity disease.

A preferred method for enhancing expression of the major histocompatibility complex molecules is by subjecting the preparation containing the antigen presenting cells to room temperature. Alternate methods of treatment of the antigen presenting cells also are provided.

According to another aspect of the invention, a method for making a pharmaceutical preparation for administration to a mammal is provided. The method comprises placing the above-described antigen-associated antigen presenting cell, or components of same, in a pharmaceutically acceptable carrier.

According to yet another aspect of the invention, a method for specifically modifying the immune system response of a mammal to an antigen is provided. The method comprises administering the above-described pharmaceutical preparation to the mammal. In a preferred embodiment, the antigen presenting cells are isolated from a human recipient, treated and returned to the patient in the form of antigen-associated antigen presenting cells. Optionally, the pharmaceutical preparation is stored in aliquots containing an amount of antigen-associated antigen presenting cells sufficient to boost the immune response of the patient. Selection of an amount of cells necessary to boost the patient's immune response is within the capabilities of those skilled in the art without the need for undue experimentation. The amount of cells is, in part, dependent upon the patient's age, weight and medical profile. Preferably, an amount of cells ranging from a minimum of about 25,000 to a maximum of about 200×10⁶ antigen presenting cells is sufficient to boost the immune response of the patient (Ben-Nun, A., et al., "Vaccination against autoimmune encephalomyelitis with T lymphocyte line cells reactive against myelin basic protein", *Nature* 292:60–61 (1981); Holoshitz, J., et al., "Lines of T lymphocytes induce or vaccinate against autoimmune arthritis", *Science* 219:56–58 (1983); Lider, O., et al., "Anti-idiotypic network induced by T cell vaccination against experimental autoimmune encephalomyelitis", Science 239:181–183 (1988); Khavari, P., et al., "Specific vaccination against photoinactivated cloned T cells", Abstract Clin. Res. 36:662A (1988); and Edelson, R., et al. "Treatment of cutaneous T. cell lymphoma by extracorporeal photochemotherapy", *N. Engl. J. Med.* 316:297–303 (1987).

In one embodiment, treatment of the antigen presenting cells to enhance expression of the major histocompatibility complex molecules comprises irradiating the antigen presenting cells in the presence of a photoactivatable agent. In some instances, the photoactivatable agent may be administered orally to the patient prior to the enhancement step.

According to still another aspect of the invention, a pharmaceutical composition for modifying an immune system response to an antigen is provided. The composition comprises a pharmaceutically acceptable carrier and a plurality of antigen presenting cells, each cell having on its surface a major histocompatibility complex molecule associated with an antigen. In a preferred embodiment, the plurality of major histocompatibility complex molecules represent a relatively homogeneous population. The antigen presenting cells of the present invention have an elevated concentration of major histocompatibility molecules compared to corresponding, naturally occurring antigen presenting cells. The preparation contains an amount of antigen presenting cells sufficient to modify the patient's immune system response. Selection of an amount of cells necessary to modify the patient's immune response is within the capabilities of those skilled in the art without the need for undue experimentation. The amount of cells is, in part, dependent upon the patient's age, weight and medical profile. Preferably, an amount of cells ranging from a minimum of about 25,000 to a maximum of about 200×10⁶ antigen presenting cells is sufficient to boost the immune response of the patient. (Ben-Nun, A., et al., supra.; Holoshitz, J., et al., supra.; Lider, O., et al., supra.; Khavari, P., et al., supra.; and Edelson, R., et al., *N. Engl. J. Med.* 316, supra.

These and other aspects of the invention as well as various advantages and utilities will be more apparent with reference to the detailed description of the preferred embodiments and in the accompanying drawings.

DETAILED DESCRIPTION OF THE INVENTION

One method for forming an antigen-associated antigen presenting cell comprises (a) treating a preparation containing an antigen presenting cell to enhance expression of a major histocompatibility complex molecule and (b) reacting the treated antigen presenting cell with the antigen extracorporeally to form the antigen-associated antigen presenting cell.

As used herein, the term antigen includes peptides, nucleoproteins, nucleic acids, polysaccharides and analogues of these molecules. The term analogue includes the above-identified antigens which have been modified, e.g., by chemical agents or enzymatic cleavage, synthetic molecules containing all or part of the above-identified antigens, as well as hybrid molecules, e.g., molecules containing portions of at least two different antigens. The analogues are prepared using chemical or biochemical synthesis methods, e.g., by employing cloning techniques, according to methods within the ordinary skill of the art. In general, an antigen is any molecule which can potentially elicit an immune system response. Thus, the term antigen includes autologous antigens, e.g., circulating tissue antigens associated with an autoimmune disease and cancer antigens that are present in autologous cancer cells but are not expressed in a non-neoplastic state, as well as exogenous antigens.

Preferred antigens include proteins and/or peptides associated with an allergic reaction (e.g., poison ivy, penicillin), a pathological state, an immunodeficiency disease or a hypersensitivity disease. Exemplary immunodeficiency diseases include acquired immunodeficiency syndrome (AIDS), certain forms of cancer, immunodeficiency of old age, and immunodeficiency following immunosuppressive therapy. Hypersensitivity disease is broadly defined to include delayed-type hypersensitivity reaction, autoimmune disease, allergy, infectious disease, rejection of allografts, and graft-versus-host reaction. More specifically, exemplary autoimmune diseases include rheumatoid arthritis, pemphigus vulgaris, systemic sclerosis and systemic lupus erythematosus. Exemplary AIDS-related antigens include core protein p24, envelope protein gp120, gp41, gp55, and gp66/31 (Bisaccia, E. et al., supra.).

Antigens associated with a pathological state, e.g., peptides derived from a solid tumor malignancy, are isolated by surgically removing all or part of the tumor and extracting the tumor-associated antigens. In addition, tissue culture supernatants from suspensions of the malignant cells and plasma of patients with malignancy can serve as sources of the tumor associated antigens. Exemplary cancer antigens include tumor antigens such as those described by P. Boon in "Toward a Genetic Analysis of Tumor Rejection Antigens", *Adv. Cancer Res.* 58:177–210 (1992). As disclosed in Boon, supra., exemplary tumor antigens (including the respective amino acid sequences for normal and mutated forms of the antigen, respectively) include: P91A (SEQUENCE I.D. No. 1) isoleucine-serine-threonine-glutamine-asparagine-arginine-arginine-alanine-leucine-aspartic acid-valine-alanine; (SEQUENCE I.D. No. 2) isoleucine-serine-threonine-glutamine-asparagine-histidine-arginine-alanine-leucine-aspartic acid-valine alanine); P35B (SEQUENCE I.D. No. 3) (glycine-proline-histidine-serine-serine-asparagine-phenylalanine-glycine-tyrosine; (SEQUENCE I.D. No. 4) -glycine-proline-histidine-serine-asparagine-asparagine-phenylalanine-glycine-tyrosine); P198 (SEQUENCE I.D. No. 5) (lysine-tyrosine-glutamine-alanine-valine-threonine-alanine-threonine-leucine-glutamic acid-glutamic acid; (SEQUENCE I.D. No. 6) lysine-tyrosine-glutamine-alanine-valine-threonine-threonine-threonine-leucine-glutamic acid-glutamic acid); and P1A (SEQUENCE I.D. No. 7) (glutamic acid-isoleucine-leucine-proline-leucine-glycine-tryptophan-leucine-valine-phenylalanine-alanine-valine-valine; (SEQUENCE I.D. No. 8) glutamic acid-isoleucine-leucine proline-leucine-glycine-tryptophan-leucine-alanine-phenylalanine-alanine-valine-valine).

There is no requirement to purify the peptides derived from the patient's malignant cells prior to use in accordance with the method of the invention. It may be desirable, however, to do so in order to increase the concentration of the antigen on the surface of the antigen presenting cells according to the methods of the invention. Moreover, if peptide antigens are purified and sequenced, they may in certain instances then be prepared synthetically.

The term antigen also includes antigens associated with a hypersensitivity disease, and in particular, antigens associated with a hypersensitivity disease mediated by the clonal expansion of circulating aberrant T cells. In a preferred embodiment, the antigen is derived from a clonotypic T cell receptor. The present invention thus provides a method for enhancing a clone-specific immune reaction which kills or inhibits proliferation of an aberrant population of T cells.

The antigen presenting cells are contained in a preparation that is an isolate of, for example, blood, lymph fluid, bone marrow, lymphatic organ tissue or cell cultures derived therefrom. Preferably, the antigen presenting cells are normal cells, i.e., non-mutant cells, of human or synthetic origin. The term "mutant cells" as used herein, refers to cells having mutations affecting the intracellular mechanism for loading intracellular peptides into the binding clefts of newly synthesized class I molecules. In the preferred embodiments, the normal human antigen presenting cells are leukocytes, more preferably T cells. These cells may be isolated from human fluid samples, e.g., peripheral blood, according to standard procedures well known in the art.

The phrase "antigen presenting cells" refers to a class of cells capable of presenting antigen to cells of the immune system that are capable of recognizing antigen when it is associated with a major histocompatibility complex molecule. Antigen presenting cells mediate an immune response to a specific antigen by processing the antigen into a form that is capable of associating with a major histocompatibility complex molecule on the surface of the antigen presenting cell. Antigen presenting cells include such diverse cell types as macrophages, T cells and synthetic ("artificial") cells. In one embodiment, the artificial cell is a vesicle, e.g., liposome, having a lipid bilayer membrane resembling the lipid bilayer of a naturally occurring cell. The liposome further includes a major histocompatibility complex molecule associated with the lipid bilayer. These diverse cell types have in common the ability to present antigen in a form that is recognized by specific T cell receptors.

T cells include T helper cells and cytotoxic T cells. Each T cell clone expresses a different surface receptor which recognizes the antigen only when it is associated with a major histocompatibility complex molecule on the surface of the antigen presenting cell. T cells that are activated by combination with antigen and expanded by clonal proliferation mature into effector and memory cells which provide specific immunity to the antigen (*Essential Immunology*, supra. pp.28–31). Cytotoxic T cells bind antigen that is associated with major histocompatibility complex class I molecules. T helper cells recognize and bind antigen associated with major histocompatibility complex class II molecules.

The term "major histocompatibility complex molecule" refers to a molecule on an antigen presenting cell that has the ability to associate with the antigen to form an antigen-associated antigen presenting cell. Recognition of the antigen-associated presenting cell by the T cell is mediated by the T cell surface receptor. In a preferred embodiment, the major histocompatibility complex molecule is a class I or class II molecule.

The class I molecule, composed of a heavy chain and a noncovalently linked beta-2-microgluobulin molecule, includes a cleft or crevice for receiving the antigen. Accordingly, the antigen has a size and dimension that permit entry of the antigen into the crevice. The size and dimension of the crevice is known to those of ordinary skill in the art (F. Latron, "A Critical Role for Conserved Residues in the Cleft of HLA-A2 in the Presentation of a Nonapeptide to T-cells", *Science* 257:964–967 (1992)). Preferably, the antigen fits substantially within the crevice, but is still accessible to a T cell capable of recognizing the antigen when it is associated with the class I molecule. In a most preferred embodiment, the antigen is a peptide having between eight and ten amino acids, two of which amino acids are hydrophobic residues for retaining the peptide in the crevice. The peptide may, for example, be derived from a tumor, a tissue, a viral protein or a bacterial protein.

Several methods are disclosed to enhance expression of the major histocompatibility complex molecules. The simplest method of enhancement comprises temperature reduction, i.e., cooling the preparation containing the antigen presenting cells to approximately room temperature, e.g., between about 21° C. and about 28° C. Preferably, the temperature of the preparation is reduced to between 21° C. and 22° C.

It is believed that a reduction in temperature results in enhanced expression of the major histocompatibility complex class I molecules by preventing instability of "empty" class I molecules, which molecules are thermodynamically unstable at physiological temperatures. The term "enhanced expression" as used herein, refers to a cell carrying on its surface substantially more empty major histocompatibility complex molecules than would be carried on the surface of a naturally occurring cell. The term "empty" as used herein, refers to a class I molecule which is not associated with antigen. Essentially all class I molecules present at the cell surface at physiologic temperatures carry small peptides in their clefts. However, at room temperature (21°–28° C.), "empty" class I molecules are stable and available to bind appropriate extracellular peptides.

Yet another method for enhancing expression of the major histocompatibility complex molecules, and in particular, for enhancing expression of empty major histocompatibility complex molecules, is to contact the preparation with a cytokine. The term cytokine includes the molecules previously referred to as lymphokines, monokines, interleukins and interferons (*Essential Immunology, suprs.,* pp. 140–150) and includes, for example, gamma-interferon, tumor necrosis factor alpha and granulocyte monocyte colony stimulating factor, as well as molecules in the family of interleukins. Cytokines are known to increase expression of the major histocompatibility complex molecules on some antigen presenting cells, e.g., monocytes.

Yet another method for enhancing expression of the major histocompatibility complex molecules, comprises subjecting the preparation to photopheresis, i.e. irradiating the preparation in the presence of a photoactivatable agent. It is believed that photopheresis disrupts the cells' metabolic pathways responsible for processing intracellular antigen into a form that fits within the crevice defined by the major histocompatibility complex molecule. As a result of photopheresis, the major histocompatibility complex molecules on the surface of the antigen presenting cells are not saturated with antigen.

Moreover, it is believed that apoptosis, i.e., programmed cell death, by photopheresis or other means, may lead to the release of a myriad of oligopeptides and/or proteins from the apoptotic cells. These previously unseen peptides/proteins may enter and associate with the empty major histocompatibility complex molecules of the surviving cells to form non-naturally occurring species of antigen-associated antigen presenting cells, which then could be tested for their ability to confer to the recipient a beneficial immune system response.

As used herein, photopheresis refers to exposure of a preparation of antigen presenting cells to radiation in the presence of a photoactivatable agent. If the photoactivatable agent is a psoralen (described below), the radiation is preferably ultraviolet irradiation, but may be visible light (Gasparro, F., et al., "The Excitation of 8-methoxypsoralens with Visible Light. Reversed Phase HPLC Quantitation of Monoadducts and Crosslinks" (in press)). Photopheresis procedures are described in U.S. Pat. No. 5,147,289, the contents of which have been incorporated by reference. Photopheresis may be performed on a continuous stream, as described in the Edelson '289 patent, or may be performed batchwise. Briefly, continuous photopheresis comprises forming a preparation of cells into an extracorporeal stream, flowing the stream through a treatment chamber substantially transparent to ultraviolet radiation, and irradiating the stream in the chamber with ultraviolet radiation in the presence of the photoactivatable agent.

The irradiation step takes place in the presence of a photoactivatable agent. According to one aspect of the invention, the preparation of antigen presenting cells contains extracellular fluid in which the photoactivatable agent is present. According to yet another embodiment, the photoactivatable agent is present within or on the surface of the antigen presenting cell. Thus, the photoactivatable agent may be administered to the patient prior to withdrawing the antigen presenting cell material from the patient for treatment.

The photoactivatable agent may be any agent which has an affinity for an important component of the antigen presenting cell and which, upon binding to the component, enhances and/or stabilizes expression of the major histocompatibility complex molecules. Exemplary photoactivatable agents are psoralens, porphyrins, pyrenes, phthalocyanine, photoactivated cortisone, photoactivated antibodies specifically reactive with the antigen presenting cell, and monoclonal antibodies which have been linked to porphyrin molecules.

The psoralens are a preferred class of photoactivatable agents. The interactions of psoralens with the DNA, protein and lipid components of T cells have been described ("T Cell Molecular Targets for Psoralens", *Annals of N.Y. Academy of Science* 636:196–208 (1991), Malane, M. and Gasparro, F. Following oral administration, psoralens are absorbed from the digestive tract, reaching peak levels in the blood and other tissues in one to four hours and are excreted almost entirely within 24 hours following oral administration. These agents can also be added directly to the extracorporeal cell preparation. The psoralen molecules are inert prior to exposure to ultraviolet light irradiation and are transiently activated into an excited state following irradiation. These transiently activated molecules are capable of photomodifying DNA and generating other reactive species, e.g., singlet oxygen, which are capable of modifying other cellular components. Other agents, e.g., mitomycin C and cis-platinum compounds, damage DNA by crosslinking strands of the nucleic acid. However, such agents remain in an active state when returned to the patient and thus are not as desirable as the psoralens for treating cells.

Preferred psoralens include 8-methoxypsoralen (8-MOP), 4'-aminomethyl-4,5', 8-trimethyl-psoralen (AMT), 5-methoxypsoralen (5-MOP) and trimethylpsoralen (TMP). 8-MOP is both an anti-cancer drug, an immune system modulator and a prototype for the development of a class of drugs that are photoactivatable. AMT is a synthetic, water soluble analogue of 8-MOP. This and other synthetic water soluble analogues of 8-MOP are described in Berger et al., "The Medical and Biological Effects of Light", *Annals of N.Y. Academy of Science* 453:80–90 (1985). Some investigators have reported that 5-MOP is not as efficacious as 8-MOP in the treatment of psoriasis (Calzavara-Pinton, et al., *Exptl. Dermatol.* 1:46–51 (1992)). TMP is widely used to treat vitiligo patients resulting in the repigmentation of depigmented areas of skin.

Monoclonal antibodies which recognize 8-MOP-DNA photoadducts in irradiated cells may be used to determine the optimum amount of ultraviolet or visible light irradiation to achieve optimal T cell inactivation (see Yang et al., "8-MOP DNA Photoadducts in Patients Treated with 8-MOP and UVA", *J. Invest. Dermatol.* 92:59–63 (1989). The activation of selected genes during apoptosis leads to the synthesis of nucleases and proteases which ultimately participate in destruction of the cell.

The conditions for oral administration of 8-MOP are described in U.S. Pat. No. 5,147,289, the contents of which have been incorporated herein by reference. Extracorporeal exposure to a photoactivatable agent offers several advantages over oral dosage administration. Dosage levels are more easily monitored and maintained in vitro. Moreover, extracorporeally administered agents can be attached to drug carriers that would otherwise be too toxic for oral administration. Such carriers can be used to target the agent into a specific cell. For example, insulin has been used to carry large photoreactive molecules, e.g., fluorescein and psoralen, into activated T lymphocytes and monoclonal antibodies have been used to deliver liposomes with photoreactive pyrene incorporated into its membrane to target T cells (see Berger, C., et al., "Comparison of Synthetic Psoralen Derivatives and 8-MOP in the inhibition of Lymphocyte Proliferation", *Annals of N.Y. Academy of Science* 453:80–90 (1985). Such carrier mediated photoactivatable drug delivery can be used in accordance with the present invention to deliver a photoactivatable drug directly to the target antigen presenting cell.

The invention also provides a method for making a pharmaceutical preparation for administration to a mammal. The treated antigen presenting cells (having enhanced expression of the major histocompatibility complex molecules) are reacted with antigen extracorporeally to form antigen-associated antigen presenting cells. The antigen presenting cells may be placed in a pharmaceutically acceptable carrier prior to treating the cells to enhance expression, prior to reacting the treated cells with antigen extracorporeally or following formation of the antigen-associated antigen presenting cells. Preferably, the antigen presenting cells are reacted with antigen in the presence of a concentration of beta-2 microglobulin that will augment the association of the major histocompatibility complex molecules with exogenous antigen. The concentration of beta-2 microglobulin is greater than the concentration of beta-2 microglobulin that would be found in vivo. Selection of the concentration of beta-2 microglobulin required to augment the association of antigen with the major histocompatibility complex molecules is within the ordinary skill of the art. In general, an amount of beta-2 microglobulin is added to give a concentration ranging from about 2 to about 10 micrograms/ml (Rock et al., *PNAS (USA)* 87:7517–7521 (1990).

The invention further provides a method for specifically modifying the immune system response of a mammal to an antigen. The method involves administering the above-described pharmaceutical composition to the mammal. In a preferred embodiment, the antigen-associated antigen presenting cells are stored in aliquots containing an amount of antigen-associated antigen presenting cells sufficient to boost the immune response of the mammal. As described above, determination of the amount of cells necessary to boost the patient's immune response is within the ordinary skill of the art. Preferably, an amount of cells ranging from a minimum of about 25,000 to a maximum of about $200 \times 10^6$ antigen presenting cells is sufficient to boost the immune response of the patient. The amount of cells used will, in part, be dependent upon whether the antigen presenting cells are efficient, e.g., B cells or monocytes, or inefficient, e.g., T cells. According to one aspect of the invention, a photo-activatable agent is administered to a human patient prior to isolating antigen presenting cells from the patient. The antigen-associated antigen presenting cells are returned to the patient according to any appropriate mode of administration known in the art, e.g., injection into the blood stream or the immune system of the patient.

Also within the scope of the invention are pharmaceutical compositions for modifying an immune response to an antigen. The composition comprises a plurality of antigen-associated antigen presenting cells contained in a suitable pharmacologically acceptable carrier. The plurality of antigen-associated antigen presenting cells differs from the corresponding naturally occurring cells in several respects. The antigen-associated antigen presenting cells of the invention represent a relatively homogeneous population of cells. This is primarily because the antigen is in its final form when it is reacted with the antigen presenting cells, i.e., the antigen is not further processed by the antigen presenting cells prior to association with the major histocompatibility complex molecule on the surface of the antigen presenting cell. The antigen-associated antigen presenting cells of the present invention are further distinguishable from the corresponding naturally occurring cells in that the former cells have an elevated concentration of major histocompatibility complex molecules on a per cell basis. Accordingly, the antigen presenting cells of the invention advantageously present an increased number of like antigen molecules to the immune system of the patient. Preferably, the antigen is autologous, e.g., a circulating tissue antigen or a tumor associated antigen such as a peptide that is not expressed in a non-neoplastic state. In certain instances, where immunologic tolerance to an exogenous antigen (such as an allergenic drug or environmental allergens, e.g., poison ivy) is desirable, that exogenous antigen could be used. Simlarly, where an artificial cross-reactive antigen is highly stimulatory of immunization against a "self" antigen, such manufactured antigens could be added. Optionally, the pharmaceutical composition contains a concentration of beta-2 microglobulin greater than that which would be found in vivo. Selection of the concentration of beta-2 microglobulin necessary to augment association of the antigen with the major histocompatibility complex molecule is within the ordinary skill in the art. The usual concentration of beta-2 microglobulin is in the range of about 2 to about 10 ug/ml (Rock et al., supra.). The beta-2 microglobulin is included in the pharmaceutical preparation to facilitate association of the antigen with the major histocompatibility complex molecules.

EXAMPLES

The present invention provides methods and pharmaceutical compositions for modifying the immune response of a mammal to a specific antigen. There is no requirement that the antigen be isolated prior to use in accordance with the method of the invention. Accordingly, the antigen may, for example, be a peptide-containing extract derived from tissue culture fluid of a tumor. Alternatively, the antigen may be a synthetic peptide corresponding to a well defined clonotypic surface receptor for an aberrant clone of T cells. The following examples illustrate representative utilities of the present invention.

Example 1

Characterization of 8-MOP Photoadducts

The photoreactivity of psoralens towards amino acids has been examined by several investigators, however, psoralen-amino acid photoadducts have not previously been characterized. Amino acid analysis of proteins exposed to UVA-activated psoralens indicates that the targets of photomodification (but not necessarily photoaddition) are the aromatic amino acids: tyrosine, tryptophan, histidine and phenylalanine, as well as methionine.

A. Photomodification of Lysozyme (1) Direct Photomodification of Lysozyme:

Lysozyme (0.4 mg/ml) and 8-MOP (0.04 mg/ml) including trace amounts of [$^3$H]8-MOP) were exposed to UVA (3.6 mW/cm$^2$; filtered with window glass to remove UVB). Aliquots were taken after 15, 30, 60 and 120 min. UVA exposure and were dialyzed exhaustively using distilled water in a microdialyzer (BRL, Bethesda, Md.). An aliquot of each sample was analyzed by liquid scintillation analysis to determine the extent of covalent photobinding of 8-MOP. The results are presented in the following table:

| Minutes UVA exposure | moles 8-MOP/moles Lysozyme |
| --- | --- |
| 0 | 0 |
| 30 | 0.90 |
| 60 | 2.04 |
| 120 | 1.86 |

(2) Effect of Psoralen Photobinding to Lysozyme on Enzymatic Processing:

8-MOP photomodification of lysozyme resulted in altered enzymatic processing by chymotrypsin. The above-described photomodified lysozyme samples were enzymatically hydrolyzed using trypsin and/or chymotrypsin (Yale Protein Center). Trypsin recognizes a limited number of cleavage sites and accordingly, is more specific than chymotrypsin. Chymotrypsin specifically recognizes cleavage sites which include tyrosine and tryptophan residues. Thus, it was expected that psoralen photomodification of lysozyme would reduce the number of chymotrypsin fractions as a result of psoralen photoaddition to these amino acids (TYR, TRP).

Figure 1:
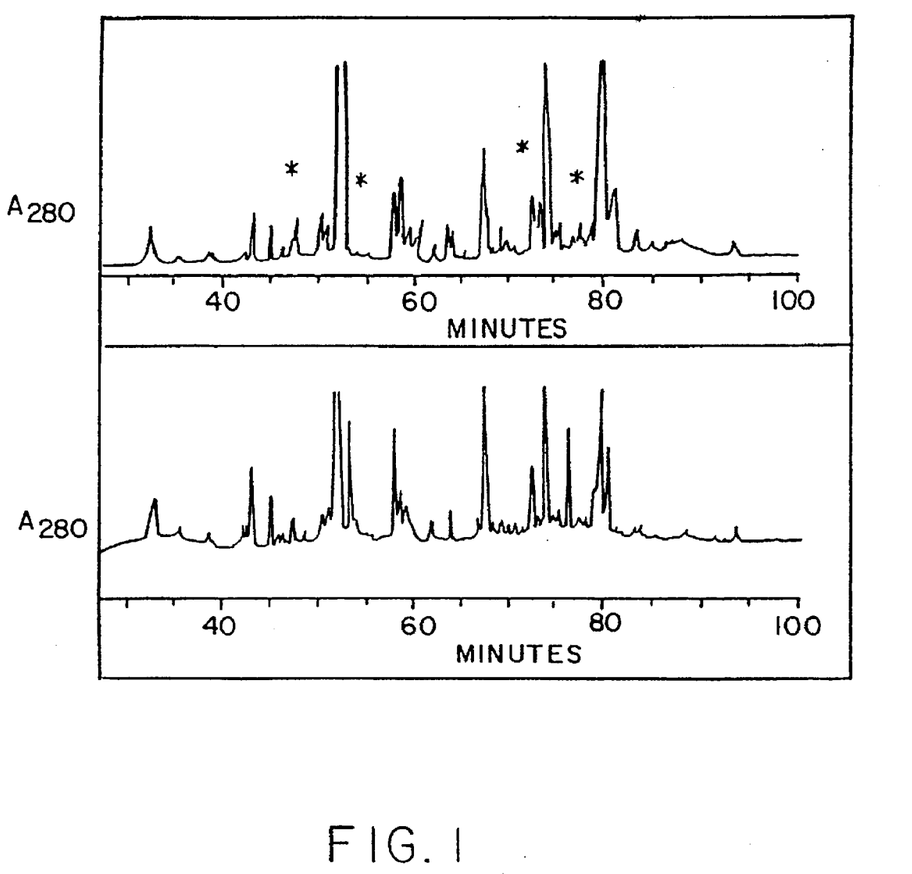
FIG. 1 illustrates the HPLC profile of oligopeptide fragments produced following the chymotrypsin cleavage of lysozyme after treatment with 8-MOP and UVA.

The HPLC results (FIG. 1) demonstrated that treatment of lysozyme with 8-MOP and UVA altered the pattern of oligopeptide fragments produced following treatment of lysozyme samples with chymotrypsin. Altered oligonucleotides are indicated with an asterisk (*) in the figure.

B. Photomodification of Chick Ovalbumin

Photobinding of 8-MOP to Chick ovalbumin amino acids was demonstrated following excitation with visible light (419 nm). Approximately 0.1% photoadducts were observed per amino acid.

Ovalbumin (0.4 mg/ml) and 8-MOP (0.04 mg/ml) containing trace amounts of [$^3$H]8-MOP) were exposed to visible radiation (419 nm) for 60 min. and thereafter, dialyzed exhaustively using distilled water in a microdialyzer (BRL, Bethesda, Md.). An aliquot of the sample was analyzed by liquid scintillation analysis. The extent of covalent photobinding of 8-MOP to ovalbumin was found to be approximately 0.039 8-MOP molecules/ovalbumin molecule.

C. Direct photomodification of an 8 amino acid oligopeptide (HIV T peptide)

An eight amino acid oligopeptide (D-ala-ser-thr-thr-thr-asn-tyr-thr-$NH_2$, (peptide T-amide HIV inhibitor) was selected for photomodification because it contained a single tyrosine that could serve as a target for 8-MOP photomodification. HIV peptide T (0.4 mg/ml) and 8-MOP (0.04 mg/ml) containing trace amounts of [3H]8-MOP) were exposed to UVA (3.5 mW/cm$^2$; filtered with window glass to remove UVB). Aliquots were taken following 15 and 30 min. UVA exposure, dialyzed exhaustively using distilled water as described above, and analyzed by liquid scintillometry. The extent of covalent photobinding of 8-MOP was determined to be as follows:

| Minutes UVA exposure | 8-MOP adducts/HIV peptide |
|---|---|
| 15 | 0.028 |
| 30 | 0.041 |

Aliquots of the treated HIV peptide were also analyzed by reversed phase HPLC (Vydac C4 reversed phase analytical column 4.6×250 mm). Unmodified HIVp eluted at approximately 16 min. using a gradient consisting of Acetonitrile (ACN) and 0.1% trifluoroacetic acid (TFA) (0–60% over a 30 minutes period). HIVp photomodified with 8-MOP eluted at about 17 min. as determined by liquid scintillation analysis of fractions collected during reversed phase analysis. The eluted oligopeptides were partially characterized using a scanning diode array detector (Spectra-Physics). Ultraviolet absorbance from 200–360 nm was monitored and accumulated by an interfaced IBM PS2/Model 60 microcomputer. Analysis of the chromatographic data can be used to provide an entire UV spectrum of any peak in the chromatogram. Unmodified oligopeptides (containing an aromatic amino acid) showed a typical "protein" spectrum with a characteristic shoulder at 280 nm and a shorter wavelength peak arising from the peptide bond absorbance. Oligopeptides containing the azido moiety showed an additional UV band near 320 nm and hence, were easily located in the HPLC chromatogram. Although not used in the above-described example, psoralens would, if used, also exhibit a longer wavelength absorbance component.

Example 2

Formation of Antigen-Associated Antigen Presenting Cells

A. Treatment of Mononuclear Leukocytes to Enhance Expression of Major Histocompatibility Complex Class I molecules Mononuclear leukocytes, containing antigen presenting cells, are withdrawn from a patient using a leukopheresis procedure. The withdrawn leukocytes are exposed to 8-MOP at a concentration of between about 1 ng/ml to about 10,000 ng/ml and to ultraviolet A or visible light to activate the photoactivatable drug at a temperature in the range of about 20° C. to about 28° C. Optionally, the treated leukocytes are contacted with agents known to increase expression of the major histocompatibility complex class I molecules, e.g., gamma interferon or tumor necrosis factor alpha.

B. Reaction of Antigen Presenting Cells with Antigen to form an Antigen-Associated Antigen Presenting Cell The treated leukocytes are allowed to react with peptides derived from any of the following sources: supernatants of autologous tumor cells in culture, chemical extracts of fresh tumor cells, autoreactive T cells, or tissue targets of autoreactive T cells. The resultant antigen-associated antigen presenting cells are placed in a pharmaceutically acceptable carrier and injected into the patient to induce an immune system response.

Example 3

Post-exposure Vaccination to Down-regulate an Immune Response—Treatment of Rheumatoid Arthritis Conventional vaccination relies upon innoculation of a patient with an antigen, e.g., an innocuous form of, an infectious agent, to establish a primary immune response. Two basic types of cells are generated during a primary immune response: effector cells for cell-mediated immunity and memory cells. Each of these Cell types originates from lymphocytes that are reactive with the antigen used for the primary immunization. Subsequent exposure to the antigen quickly boosts the level of memory cells, thereby producing high levels of antibodies specific for antigen (*Essential Immunology, supra.*, p. 27).

Post-exposure vaccination for the treatment of a hypersensitivity disease, e.g., autoimmune disease and graft-versus-host reaction associated with tissue rejection, relies upon the basic principles of conventional vaccination. However, in contrast to convention procedures, vaccination takes place following exposure of the patient's immune system to antigen.

Patients suffering from rheumatoid arthritis have in their blood T cells that are reactive with a protein component of the patient's, joints. Two alternative strategies are employed to treat a disease such as rheumatoid arthritis: (A) clonal anergy to effectively paralyze the patient's immune system response and (B) induction of the patient's immune response against the T cells which initiate the disease.

(A) Clonal anergy to paralyze the patient's immune system response to an existing immune population of unwanted effector cells:

The relevant autoantigen(s) are obtained, for example, by synthesis (if the autoantigen has previously been characterized) or by preparing a biological extract derived from a tissue or cell source believed to contain the autoantigen, e.g., an extract of a synovial biopsy. A preparation containing the relevant autoantigen(s) against which the aberrant immune response is directed, is reacted with the patient's antigen presenting cells that have been treated to exhibit enhanced expression of empty class I molecules. The antigen presenting cells are characterized in that they lack the capacity to send the co-stimulatory (second) signal(s) required for a T cell mediated immune response. Thus, antigen presenting cells are selected which naturally lack the capacity to send the second signal, e.g., normal T cells, or antigen presenting cells initially having the capacity to send the second signal are deprived of that capacity by, e.g., treatment with fixation agents, exposure to UVB irradiation, or exposure to 8-MOP in the presence of UVA irradiation.

As a result of immunization of the patient with the antigen-associated antigen presenting cell, the patient produces cytotoxic T cells. These cytotoxic cells recognize the antigen presenting cells containing the joint protein-derived peptide antigen associated with major histocompatibility complex class I molecules. However, because the antigen presenting cells are unable to send the second signal necessary for an immune response, the patient's cytotoxic T cells are effectively paralyzed, i.e., clonal anergy, and an autoimmune response directed at the patient's joint is preempted.

(B) Induction of an Anti-idiotypic Suppressor Response:

An alternative strategy to treat a disease such as rheumatoid arthritis is to induce the patient's immune response against the T cells which initiate the disease, presumably due to the T cells ability to recognize an autoantigen(s) in the patient's joints, i.e., to induce an anti-idiotypic suppressor response.

In accordance with this treatment strategy, a preparation containing peptides or proteins corresponding to the receptors of the patient's aberrant, i.e., autoreactive, T cells is prepared. The T cell receptor peptides are reacted with antigen presenting cells ex vivo and returned to the patient. In contrast to the above-described strategy directed to inducing clonal anergy, this alternative strategy employs antigen presenting cells which have the capacity to send the co-stimulatory signals. Thus, following reinfusion of the antigen-associated antigen presenting cells, the patient's immune response is induced against the aberrant clone of T cells.

Example 4

Post-exposure Vaccination to Down-regulate an Immune Response—Prevention of Allograft Rejection Transplant rejection occurs when the patient's immune system attacks antigenic determinants, e.g., peptides, present on donor cells. Such rejection is circumvented by tolerizing the patient to these peptide antigens prior to transplantation. An intended recipient of a tissue transplant, e.g., a renal allograft, is tolerized to the donor tissue in an analogous manner to that described above with respect to treating rheumatoid arthritis. Accordingly, the patient's antigen presenting cells are treated to maximize expression of class I molecules and are incubated with donor tissue cells, e.g., peripheral blood cells, that have been expanded in vitro. The antigenic peptides of the donor cells associate with the class I molecules, forming antigen-associated antigen presenting cells. The antigen presenting cells are treated in such a way as to deprive them of their co-stimulatory signals by, for example, treatment with fixation agents, exposure to UVB irradiation, or treatment with 8-MOP in the presence of UVA irradiation. Prior to transplantation, these antigen-presenting cells are placed in a pharmaceutically acceptable carrier and are injected into the patient, thereby tolerizing those cells potentially able to respond to donor antigens. When the donor kidney is transplanted, the patient's immune system does not mount an immune response because the patient has previously been tolerized to the presence of the donor's distinctive antigenic peptides.

Example 5

Post-exposure Vaccination to Down-Regulate an Immune Response—Prevention of Allergic Contact Dermatitis Contact dermatitis occurs when a chemical substance comes in direct contact with the skin, causing an inflammatory response with varying degrees of damage to the skin and varying symptoms including itching. Allergic contact dermatitis (ACD) is a T cell-mediated, delayed-type hypersensitivity reaction which occurs in the skin of susceptible individuals as a result of immunologically specific sensitization (immunization) and then re-exposure to topically applied allergens. These allergens are typically small molecular weight, highly chemically reactive substances (called haptens) which are capable of combining with host proteins to form complete antigens which can be recognized by T cells. The broad range of chemicals capable of inducing ACD is well documented (Fisher, A. A., *Contact Dermatitis*, 2nd Edition, Philadelphia: Lea & Febiger, 1973.)

It has been well documented that if immune T cells are exposed to antigen presenting cells (APC) which express the specific antigen/MHC complex recognized by their T cell receptors, but which fail to express appropriate second signals (i.e., appropriate co-stimulatory cytokines or cell surface molecules), then not only will the immune T cells fail to respond by proliferating and releasing pro-inflammatory cytokines, but they will be rendered anergic. That is, for a substantial period of time (perhaps weeks) such T cells will also be unable to respond to fully competent APCs expressing both the appropriate antigen/MHC (1st signal) but also the appropriate co-stimulatory (2nd) signals (Jenkins, Marc K., *Immunology Today* 13:69–73, 1992). Other studies have shown that exposure of otherwise competent, antigen-pulsed APCs to ultraviolet B radiation not only renders such cells incapable of stimulating some subsets of immune T cells, but that such T cells are rendered anergic as a result of this exposure to UVB-treated APCs (Gerometta, J. S., Takashima, A., Simon, J., Edelbaum, Do, Beergstresser, P., Mueller, D., and Cruz, Jr., P. D., "UVB radiation inactivates a co-stimulatory factor expressed on the surface of Langerhans cells, thus rendering them capable of inducing clonal anergy in CD4+ cells," *J. Invest. Dermatol.* 96:626 (abstract), 1991. Finally, a very recent report (H. P. van Iperen and G. M. J. Beijersbergen van Henegouwen, "An animal model for extracorporeal photochemotherapy based on contact hypersensitivity," *J. Photchem. Photobiol. B: Biol.* 15:361–366, 1992) has provided evidence in an animal model of allergic contact dermatitis that vaccination of immune mice with 8-MOP and UVA-treated lymph node cells from immunized donors (the lymph nodes contain both immune T cells and antigen-pulsed APCs) results in the rapid (within one week) loss of immunity to the allergen, such that subsequent application of the allergen to the skin of treated mice results in minimal evidence of allergic contact dermatitis. The rapidity of induction of unresponsiveness suggests that the mechanism of immunologic unresponsiveness operative in treated animals is clonal anergy (a possibility not considered by the authors).

Accordingly, aliquots of peripheral blood cells (including antigen presenting cells) are removed from allergic individuals, exposed to the relevant allergen, and treated in such a way (e.g., exposure to 8-MOP in the presence UVA radiation) as to render them incapable of delivering the co-stimulatory second signal to immune T cells. These antigen-associated antigen presenting cells are then placed in a pharmaceutically acceptable carrier and reintroduced into the patient.

It should be understood that the preceding is merely a detailed description of certain preferred embodiments. It therefore should be apparent to those skilled in the art that various modifications and equivalents can be made without departing from the spirit or scope of the invention.

What is claimed is:

1. A method for forming a peptide antigen-associated leukocyte, comprising the steps of:
   (a) irradiating a preparation containing a mixture of leukocytes in the presence of a psoralen at a temperature between about 20° C. and about 28° C., wherein the mixture of leukocytes is withdrawn from a mammal; and followed by
   (b) extracorporeally reacting the irradiated mixture of leukocytes with a mixture of autologous peptide antigens associated with autoimmune disease, allergic reactions, or hypersensitivity disease to form a plurality of the peptide antigen-associated leukocytes, wherein the autologous peptide antigens are obtained from said mammal.

2. The method of claim 1, wherein the leukocytes are of human origin.

3. The method of claim 1, wherein the psoralen is selected from the group consisting of 8-methoxy psoralen, aminomethyl-trimethyl psoralen, 5-methoxy psoralen and trimethyl psoralen.

4. The method of claim 3, wherein the psoralen is 8-methoxy psoralen.

5. The method of claim 1, wherein the preparation containing a mixture of leukocytes is subjected to a temperature between about 21° C. and about 22° C.

6. The method of claim 1, wherein the peptide antigens are from a clonotypic T cell.

7. A method for making a pharmaceutical preparation for administration to a mammal, comprising the steps of:
   (a) irradiating a preparation containing a mixture of leukocytes in the presence of a psoralen at a temperature between about 20° C. and about 28° C., wherein the mixture of leukocytes is withdrawn from said mammal; followed by
   (b) extracorporeally reacting the irradiated mixture of leukocytes with a mixture of autologous peptide antigens associated with autoimmune disease, allergic reactions, or hypersensitivity disease to form a plurality of the peptide antigen-associated leukocytes, wherein the autologous peptide antigens are obtained from said mammal; and
   (c) placing the peptide antigen-associated leukocytes in a pharmaceutically acceptable carrier.

8. A method for specifically down-regulating the immune system T-cell response of a mammal to an autologous peptide antigen, comprising the steps of:
   (a) irradiating a preparation containing a mixture of leukocytes in the presence of a psoralen at a temperature between about 20° C. and about 28° C. wherein the mixture of leukocytes is withdrawn from said mammal; followed by
   (b) extracorporeally reacting the irradiated mixture of leukocytes with a mixture of autologous peptide antigens associated with autoimmune disease allergic reactions, or hypersensitivity disease to form a plurality of peptide antigen-associated leukocytes, wherein the autologous peptide antigens are obtained from said mammal; and
   (c) administering the peptide antigen-associated leukocytes to said mammal.

9. The method of claim 8, further comprising the step of adding beta-2 microglobulin to the irradiated leukocytes when the irradiated leukocytes are reacted with the plurality of peptide antigens.

10. The method of claim 8, further comprising the step of storing the peptide antigen-associated leukocytes prior to administering the peptide antigen-associated leukocytes to the mammal.

11. The method of claim 10, wherein the peptide antigen-associated leukocytes are stored in aliquots containing a concentration of peptide antigen-associated leukocytes sufficient to boost the immune response of the mammal.

12. A method for specifically down-regulating the immune system T-cell response of a mammal to an autologous peptide antigen of said mammal, comprising the steps of:
   (a) withdrawing a mixture of leukocytes from said mammal;
   (b) irradiating the mixture of leukocytes in the presence of a psoralen at a temperature between about 20° C. and about 28° C.; followed by
   (c) extracorporeally contacting the irradiated mixture of leukocytes with a mixture of autologous peptide antigens associated with autoimmune disease, allergic reactions, or hypersensitivity disease to form a plurality of autologous peptide antigen-associated leukocytes; and
   (c) administering the autologous peptide antigen-associated leukocytes to said mammal.

* * * * *